United States Patent
Frenkel et al.

(10) Patent No.: US 9,745,450 B2
(45) Date of Patent: Aug. 29, 2017

(54) STABILIZERS CONTAINING HIGH PURITY MONO-OCTYLTIN COMPOUNDS

(71) Applicant: Galata Chemicals LLC, Southbury, CT (US)

(72) Inventors: Peter Frenkel, Danbury, CT (US); Johannes Kaufhold, Wattenheim (DE)

(73) Assignee: Galata Chemicals LLC, Southbury, CT (US)

( * ) Notice: Subject to any disclaimer, the term of this patent is extended or adjusted under 35 U.S.C. 154(b) by 0 days.

(21) Appl. No.: 15/266,379

(22) Filed: Sep. 15, 2016

(65) Prior Publication Data

US 2017/0002180 A1 Jan. 5, 2017

Related U.S. Application Data

(63) Continuation of application No. PCT/US2016/026133, filed on Apr. 6, 2016.

(60) Provisional application No. 62/171,415, filed on Jun. 5, 2015.

(51) Int. Cl.
*C08K 5/58* (2006.01)
*C07F 7/22* (2006.01)

(52) U.S. Cl.
CPC ............ *C08K 5/58* (2013.01); *C07F 7/22* (2013.01); *C08K 2201/014* (2013.01)

(58) Field of Classification Search
CPC ...................................................... C08K 5/58
See application file for complete search history.

(56) References Cited

U.S. PATENT DOCUMENTS

| 4,052,427 A | 10/1977 | Leistner et al. |
| 4,193,913 A | 3/1980 | Abeler |
| 4,496,490 A | 1/1985 | Larkin |
| 5,925,696 A | 7/1999 | Wehner et al. |
| 8,198,352 B2 | 6/2012 | Deelman et al. |
| 2016/0194478 A1* | 7/2016 | Frenkel ............. C07F 7/2268 524/181 |

FOREIGN PATENT DOCUMENTS

| EP | 1225177 A1 | 7/2002 |
| EP | 1743898 A1 | 1/2007 |
| EP | 2123659 A1 | 11/2009 |
| GB | 1346999 A | 2/1974 |
| GB | 1510973 A | 5/1978 |
| WO | 2009/138474 A1 | 11/2009 |
| WO | 2015/020762 A1 | 2/2015 |

OTHER PUBLICATIONS

PCT International Search Report and Written Opinion mailed Jun. 9, 2016 from corresponding Application No. PCT/US2016/026133, 10 pages.

* cited by examiner

*Primary Examiner* — Robert Harlan
(74) *Attorney, Agent, or Firm* — Dilworth IP LLC

(57) ABSTRACT

A heat stabilizer composition comprising a) at least one mono-octyltin compound $(n\text{-}Oc)Sn(T)_3$ having a purity greater than 85 wt %; and b) at least one di-methyltin compound $(Me)_2Sn(T)_2$ having a purity greater than 85 wt %.

14 Claims, No Drawings

STABILIZERS CONTAINING HIGH PURITY MONO-OCTYLTIN COMPOUNDS

FIELD OF THE INVENTION

The present invention relates to tin-based stabilizer compositions. More particularly, the present invention relates to stabilizer compositions comprising high purity mono-octyltin compounds and high purity dimethyltin compounds for chlorine-containing polymers.

BACKGROUND OF THE INVENTION

Polyvinyl chloride ("PVC") is in wide commercial use because of its superior performance and properties. Modern consumers utilize PVC-containing products throughout their daily activities, since it is a primary ingredient in profiles, sidings, floorings, films/sheets, fabrics, pipes, fittings and fabrics. Various additives, such as heat stabilizers are commonly included when formulating compositions containing PVC. Heat stabilizers are required because as PVC is heated to temperatures of 160° C. and above, decomposition reactions begin, where the polymer releases HCl. As such decomposition continues, unstable structures are formed, which further accelerate HCl elimination and decomposition. Efforts have been ongoing to develop improved heat stabilizers.

U.S. Pat. No. 8,198,352 discloses that tin-based stabilizers are used in chlorine-containing polymers and copolymers, such as PVC. The tin-based stabilizers are used as mixtures of mono-alkyltin with di-alkyltin compounds of the same alkyl group, such as mixtures of mono- and dimethyltin compounds, mono- and di-butyltin compounds or mono- and di-octyltin compounds. Tri-alkyltin compounds are known to be inefficient as heat stabilizers and their concentration in the stabilizers is usually less than 1%.

EP 2123659 discloses high purity mono-alkyltin compounds containing mono-alkyltin compounds of 95-99.99% purity, 0.01-0.5% dialkyltin compounds and 0.01-0.5% trialkyltin compounds.

U.S. Pat. No. 4,496,490 discloses the preparation of high purity mono-octyltin thioglycolate heat stabilizers starting from mono-octyltin chloride of 99.2% purity. While the product contained up to 5% tri-octyltin iso-octylmercaptoacetate, the presence of di-octyltin compounds in the final product was not reported.

U.S. Pat. No. 4,193,913 discloses high purity mono-alkyltin stabilizers prepared using mono-methyl-, mono-butyl or mono-octyltin chlorides as raw materials, and reacting those with thioglycolate esters. Purity of the chlorides was not specified.

EP 1743898 discloses preparation of mono-alkyltin and dialkyltin chlorides. While di-octyltin chloride was obtained at the purity of greater than 98%, purity of the mono-alkyltinchloride was not measured.

EP 1225177 discloses preparation of mono-alkyl in halides at greater than 60% yield, using a variety of catalysts.

GB 1510973 discloses preparation of mono-octyltin thioglycolate stabilizers using mono-octyltin chloride of 99.2% purity. Purity of the prepared mono-octyltin stabilizer was not measured or disclosed.

U.S. Pat. No. 4,052,427 discloses the preparation of dialkyltin halides and mixed dialkyltin halides, and the corresponding mixed di-alkyltin stabilizer compounds. Nevertheless, a continuing need exists for more effective, non-toxic alkyltin heat stabilizer compositions for chlorine-containing polymers.

SUMMARY OF THE INVENTION

The subject matter of the present disclosure relates to stabilizer compositions for chlorine-containing polymers. In one embodiment, the present disclosure provides a heat stabilizer composition comprising a) at least one mono-octyltin compound (n-Oc)Sn(T)$_3$ having a purity greater than 85%; and b) at least one di-methyltin compound (Me)$_2$Sn(T)$_2$ having a purity greater than 85%.

In another embodiment, the present disclosure provides a stabilized chlorine-containing polymer compound comprising a chlorine-containing polymer and a heat stabilizer composition, the heat stabilizer composition comprising: a) at least one mono-octyltin compound (n-Oc)Sn(T)$_3$ having a purity greater than 85%; and b) at least one di-methyltin compound (Me)$_2$Sn(T)$_2$ having a purity greater than 85%.

In still another embodiment, the present disclosure provides a process comprising blending a chlorine-containing polymer and a heat stabilizer composition comprising a) at least one mono-octyltin compound (n-Oc)Sn(T)$_3$ having a purity greater than 85 wt %; and b) at least one di-methyltin compound (Me)$_2$Sn(T)$_2$ having a purity greater than 85 wt %.

DETAILED DESCRIPTION OF THE INVENTION

The subject matter of the present disclosure provides a heat stabilizer composition comprising at least one mono-octyltin compound (n-Oc)Sn(T)$_3$ of high purity (>85 wt %); and at least one di-methyltin compound (Me)$_2$Sn(T)$_2$ of high purity (>85 wt %).

Chlorine-Containing Polymers

It has surprisingly been found that high purity dimethyltin compounds synergistically enhance the heat stabilizing performance of high purity mono-octyltin compounds in chlorine-containing polymers. For the purpose of this specification, the tem chlorine-containing polymers is intended to include homopolymers and copolymers of vinyl chloride, i.e., vinyl resins containing vinyl chloride units in their structure, e.g., copolymers of vinyl chloride and vinyl esters of aliphatic acids, in particular vinyl acetate; copolymers of vinyl chloride with esters of acrylic and methacrylic acid and with acrylonitrile; copolymers of vinyl chloride with diene compounds and unsaturated dicarboxylic acids or anhydrides thereof; such as copolymers of vinyl chloride with diethyl maleate, diethyl fumarate or maleic anhydride; post-chlorinated polymers and copolymers of vinyl chloride; copolymers of vinyl chloride and vinylidene chloride with unsaturated aldehydes, ketones and others, such as acrolein, crotonaldehyde, vinyl methyl ketone, vinyl methyl ether, vinyl isobutyl ether, and the like. Preferably, the chlorine-containing polymer is PVC.

The term PVC as employed herein is also intended to include graft polymers of PVC with ethyl-vinyl acetate ("EVA"), acrylonitrile/butadiene-styrene ("ABS"), and meth-acrylate-butadiene-styrene ("MBS"). Preferred substrates are also mixtures of the above-mentioned homopolymers and copolymers, preferably vinyl chloride homopolymers, with other thermoplastic and/or elastomeric polymers, more preferably blends with ABS, MBS, acrylonitrile butadiene ("NBR"), styrene-acrylonitrile ("SAN"), EVA, chlorinated polyethylene ("CPE"), poly(methyl methylacrylate), ethylene propylene diene monomer ("EPDM"), and polylactones. Preferably, vinyl acetate, vinylidene dichloride, acrylonitrile, chlorofluoroethylene and/or the esters of acrylic, fumaric, maleic and/or itaconic acids are monomers that are copolymerizable with vinyl chloride. Polymeric materials stabilized with the stabilizers of this invention also include chlorinated polyvinyl chloride (CPVC).

The PVC can be obtained via polymerization in bulk or in suspension, in emulsion, in micro suspension, or in suspended emulsion.

Heat Stabilizer Compositions

The heat stabilizer compositions of the present disclosure contain:

a) at least one mono-octyltin compound $(n-Oc)Sn(T)_3$ having a purity of greater than 85%, where for the purposes of this specification, mono-octyltin purity means the percentage of the $(n-Oc)Sn(T)_3$ material in the total weight of the octyltin-based compounds, the remainder being impurities, as discussed below.

b) at least one di-methyltin compound $(Me)_2Sn(T)_2$ having a purity of greater than 85%, where for the purposes of this specification, di-methyltin compound purity means the percentage of the $(Me)_2Sn(T)_2$ material in the total weight of the methyltin-based compounds, the remainder being impurities, as discussed below.

The weight ratio of (mono-octyltin compound)/(di-methyltin compound) ranges from 10/90 to 90/10. Preferably, the weight ratio ranges from 10/90 to 60/40.

The high purity dimethyltin compounds are prepared separately from the high purity mono-octyltin compounds and then blended together within a broad range of temperatures, preferably in a temperature range of 10 to 70° C. The purity of the mono-octyltin compounds of the present subject matter is greater than 85 wt %, preferably, greater than 90 wt %, more preferably, in the range of 92 to 99 wt %. The purity of the dimethyltin compounds of the present subject matter is also greater than 85 wt %, preferably greater than 90 wt %, more preferably in the range of 92 to 99 wt %.

Impurities that may be found in the heat stabilizer composition are dioctyltin compounds at a level of less than 8 wt %, preferably, in a range of 0.1 to 5 wt %; mono-methyltin compounds at a level of less than 8 wt %, preferably, in a range of 1 to 7 wt %; tri-methyltin compounds at a level of less than 1 wt %; and tri-octyltin compounds at a level of less than 1 wt %. Impurities may also be found as residues from the preparation process of the composition, such as ligand precursors, ligand precursor-hydrolysed by-products, tin halides, solvents, alkenes, alkyl halides, catalysts or catalyst components, decomposed catalysts or catalyst components, water, neutralization salts, and the like.

T is any ligand known in the art, the precursor of which is H-T. H-T compounds may be selected from among H—$SCH_2CH_2OH$, H—$SCH_2$—$CH(OH)$—$CH_3$, H—$SCH_2COOR_1$, H—$SCH_2CH_2O$—$COR_2$, H—$SR_2$, H—OH, H—$OOCR_2$, and H—$OOCR_3$—$COOR_2$, wherein $R_1$ represents $C_1$-$C_{14}$ alkyl, $R_2$ represents $C_2$-$C_{18}$ alkyl, alkenyl, aryl or alkaryl, $R_3$ represents —CH=CH—; or —$CH_2$—$R_4$—$CH_2$—, with $R_4$ representing $C_2$-$C_6$ alkylene.

Preferably, T is chosen from mercaptoacetate esters, 2-ethylhexylmercaptoacetate esters, iso-octylmercaptoacetates, iso-butylmercaptoacetates, mercaptoacetate itself, or carboxylates, maleates, diketonates, or alcoholates. More preferably, T is 2-ethylhexylmercaptoacetate (EHMA).

In the formulas $(n-Oc)Sn(T)_3$ and $(Me)_2Sn(T)_2$, each T may be identical or different from each other. Preferably, all ligands T are identical, More preferably, the compound of formula $(n-Oc)Sn(T)_3$ is (n-Octyl)Sn[tris(2-ethylhexyl-mercaptoacetate)], while the compound of formula $(Me)_2Sn(T)_2$ is di(Methyl)Sn[bis(2-ethylhexyl-mercaptoacetate)].

According to another embodiment, the subject matter of the present disclosure relates to the process of preparing the above-described tin-based compositions. High purity mono-octyltin-based compounds of formula $(n-Oc)Sn(T)_3$ in which T is as defined above, are prepared from the corresponding mono-octyltin trihalides of formula $(n-Oc)Sn(Hal)_3$ in which Hal is chosen from chlorine, bromine and iodine, Preferably, Hal is chlorine. High purity di-methyltin-based compounds of formula $(Me)_2Sn(T)_2$, in which T is as defined above, are prepared from the corresponding dimethyltin dihalides of formula $(Me)_2Sn(Hal)_2$, in which Hal is chosen from chlorine, bromine and iodine. Preferably, Hal is chlorine.

In still another embodiment, the present disclosure provides a process comprising blending a chlorine-containing polymer and a heat stabilizer composition comprising a) at least one mono-octyltin compound $(n-Oc)Sn(T)_3$ having a purity greater than 85 wt %; and b) at least one di-methyltin compound $(Me)_2Sn(T)_2$ having a purity greater than 85 wt %. One skilled in the art would recognize that all conventional compounding equipment can be used to blend the materials.

Co-Stabilizers

The heat stabilizers of the present disclosure can be used in combination with co-stabilizers selected from metal salts, uracil-based heavy metals free stabilizers or mixtures thereof.

Metal salts that can be used as stabilizers in the chlorine-containing compounds include metal carboxylates of relatively long chain carboxylic acids or dicarboxylic acids. Examples include stearates and laurates, and oleates, salts of shorter-chain alkanecarboxylic acids and adipates. Metal salts can also include alkylbeozoic acids. The metals can include Li, Na, K, Mg, Ca, Sr, Ba, Zn, Al, La, Ce and rare earth metals. Synergistic mixtures, such as barium/zinc, magnesium/zinc, calcium/zinc or calcium/magnesium/zinc stabilizers can also be used. The metal salts can be used individually or in mixtures. Preferably, the metal salts can be selected from the zinc, calcium, magnesium or barium salts of monovalent carboxylic acids such as octanoic, neodecanoic, 2-ethylhexanoic, decanoic, undecanoic, dodecanoic, tridecanoic, myristic, palmitic, isostearic, stearic, 12-hydroxystearic, behenic, and sorbic acid; and calcium, magnesium and zinc salts of divalent carboxylic acids, such as oxalic, malonic, succinic, glutaric, adipic, fumaric, phthalic, isophthalic, terephthalic, hydroxyphthalic acid and citric acid.

More preferably, the metal salts are selected from the calcium, magnesium, barium and zinc carboxylates of carboxylic acids having 7 to 18 carbon atoms. Overbased carboxylates, such as overbased zinc octoate, are also preferred. Overbased calcium or barium salts are also preferred.

The metal salts can also include dimetallic salts of dicarboxylic acids such as dilithium, disodium or dipotassium salts of divalent carboxylic acids such as of oxalic, malonic, succinic, glutaric, adipic, fumaric, pentane-1,5-dicarboxylic, hexane-1,6-dicarboxylic, heptane-1,7-dicarboxylic, octane- 1,8-dicarboxylic, phthalic, isophthalic and terephthalic. Preferably, the soap is disodium adipate.

Uracil-based heavy metal-free stabilizers are described in U.S. Pat. No. 5,925,696, the disclosure of which is hereby incorporated by reference.

Examples

The following examples further detail and explain the performance of the inventive compositions. Those skilled in the art will recognize many variations that are within the spirit of the invention and scope of the claims.

Raw Materials, Test Methods and Sample Preparation

Mono-octyltin tris(2-ethylhexyl mercaptoacetate) ("MOTE") manufactured by Galata Chemicals GmbH as Mark 21 MOK-A (purity 95%); dimethyltin bis(2-ethylhexyl mercaptoacetate) ("DMTE") manufactured by Galata Chemicals LLC as Mark 1982 (purity 95%). Both materials contained the corresponding tri-alkyltin components at less than 1%. The components were blended at ambient temperature at the specified weight ratios.

PVC Compounding

The stabilizers of the current subject matter were compounded with other components into a) a clear rigid film compound that is subjected to the calendaring processing and b) a compact sheet compound that is subjected to the extrusion processing. The compounds were tested for both the static heat stability using a Mathis oven, and the dynamic heat stability using a Collin two roll mill at 190° C., while taking representative samples every 5 minutes.

Clear Rigid PVC Film Compound Testing

Control Examples 1 and 2, and Examples 3-5 for clear rigid PVC film compound testing were prepared by blending various heat stabilizer compositions at a level of 1.5 parts stabilizer per 100 parts PVC compound ("phr") with a clear rigid PVC compound. The clear rigid PVC film compound contained 100 parts Evipol SH 6030 (S-PVC resin from Ineos), 0.5 parts external lubricant, 1.0 part internal lubricant (both from Emery), 6 parts Impact Modifier (MBS type from Kaneka), and 1.2 parts of the Paraloid K 175 (acrylic processing aid from Dow Chemical). The stabilizer blends used for Control Examples 1 and 2, and Examples 3-5 are shown in Table 1.

TABLE 1

| Stabilizer components, % | Control Example 1 | Control Example 2 | Example 3 | Example 4 | Example 5 |
|---|---|---|---|---|---|
| DMTE | 100 | | 50 | 60 | 80 |
| MOTE | | 100 | 50 | 40 | 20 |

Control Examples 6 and 7, and Examples 8-10 were prepared by blending various heat stabilizer compositions with a clear, rigid PVC compound for film testing as with Control Examples 1-2 and Examples 3-5, except that the heat stabilizer was added in an amount of 1.2 phr. The stabilizer blends for Control Example 6 and 7, and Examples 8-10 are shown in Table 2.

TABLE 2

| Stabilizer components, % | Control Example 6 | Control Example 7 | Example 8 | Example 9 | Example 10 |
|---|---|---|---|---|---|
| DMTE | 100 | | 50 | 60 | 80 |
| MOTE | | 100 | 50 | 40 | 20 |

The calculated tin contents for the organotin stabilizers of the examples are shown in Table 3.

TABLE 3

| Stabilizer compositions | DMTE | MOTE | 50/50 DMTE/MOTE | 60/40 DMTE/MOTE | 80/20 DMTE/MOTE |
|---|---|---|---|---|---|
| Calculated tin content, % | 21.4 | 14.1 | 17.7 | 18.4 | 19.9 |

Normally, heat stability imparted by an organotin stabilizer on PVC is proportional to the tin content introduced with the stabilizer, Therefore, the Yellowness Index (intensity of the yellow color) of the processed PVC would be expected to decrease with the increase in tin content of the tested stabilizers, resulting in the following order: MOTE>50/50 DMTE/MOTE>60/40 DMTE/MOTE>80/20 DMTE/MOTE>DMTE Static and dynamic heat stability testing was performed on the above examples. Results are shown in Tables 4-7.

Static Heat Stability Test

A dry blend consisting of the base formulation and the stabilizers was mixed and homogenized on a mixer roll for 5 minutes at 180° C. Subsequently, test samples of 0.4 mm thickness were cut out of the center of the sheet and subjected to heat in a Mathis Thermotester Oven at 190° C. Yellowness Index was measured according to ASTM D1925-70 at 5-minutes intervals. Lower values denote minor discoloration, high values denote significant discoloration of the samples, so that the smaller the discoloration the more effective the stabilizer composition.

Dynamic Heat Stability Test Method

A dry blend consisting of the base formulation and the stabilizers was mixed and homogenized on a mixer roll for 5 minutes at 180° C. Subsequently, test samples of 0.4 mm thickness were cut out of the center of the sheet at intervals of 3 minutes. Yellowness Index was measured according to ASTM D1925-70 at 190° C. in 3-minute intervals. Higher Yellowness Index values indicate about stronger discoloration and lower stabilizer effectiveness.

The results of static heat stability (in Yellowness Index) testing for Control Examples 1-2 and Examples 3-5 are summarized in Table 4.

TABLE 4

| Time, min. | Control Example 1 | Control Example 2 | Example 3 | Example 4 | Example 5 |
|---|---|---|---|---|---|
| 0 | 7.95 | 5.32 | 4.44 | 5.59 | 4.18 |
| 5 | 8.52 | 4.78 | 4.08 | 4.41 | 6.34 |
| 10 | 8.95 | 4.48 | 5.76 | 5.40 | 6.42 |
| 15 | 9.67 | 6.21 | 6.19 | 6.18 | 6.92 |
| 20 | 10.86 | 9.78 | 7.86 | 6.16 | 7.77 |
| 25 | 13.23 | 12.95 | 9.87 | 8.55 | 8.25 |
| 30 | 13.04 | 19.02 | 12.20 | 9.41 | 10.28 |
| 35 | 15.62 | 25.10 | 15.33 | 10.97 | 12.06 |
| 40 | 18.62 | 35.86 | 19.18 | 15.70 | 15.64 |

TABLE 4-continued

| Time, min. | Control Example 1 | Control Example 2 | Example 3 | Example 4 | Example 5 |
|---|---|---|---|---|---|
| 45 | 25.17 | 44.95 | 24.18 | 21.07 | 21.24 |
| 50 | 34.55 | 57.69 | 32.25 | 27.33 | 28.04 |
| 55 | 46.37 | 72.95 | 42.76 | 37.37 | 37.99 |
| 60 | 63.24 | 85.73 | 58.84 | 50.68 | 51.03 |
| 65 | 86.58 | 97.20 | 78.24 | 65.20 | 69.92 |
| 70 | 120.57 | 106.69 | 99.03 | 86.16 | 101.02 |
| 75 | | | 115.02 | 107.03 | 122.85 |

The MOTE/DMTE blends (Examples 3-5) were found to be more effective and efficient heat stabilizers in terms of initial (0-20 min test), mid-term (20-50 min test) and long-term. (>50 min. test) static heat stability relative to individual components (Control Examples 1-2) added at 1.5 parts into the PVC film compounds, Example 4 (60/40 DMTE/MOTE) was the most effective (Table 4). This result is unexpected, since the calculated tin content of these blends is lower than that of pure DMTE (Table 3).

The static heat stability results (in Yellowness Index) for Control Examples 6-7 and Examples 8-10 are shown in Table 5.

TABLE 5

| Time, min. | Control Example 6 | Control Example 7 | Example 8 | Example 9 | Example 10 |
|---|---|---|---|---|---|
| 0 | 12.42 | 5.38 | 5.69 | 6.46 | 6.57 |
| 5 | 11.77 | 6.49 | 5.48 | 5.34 | 6.17 |
| 10 | 11.34 | 7.25 | 5.13 | 4.62 | 6.28 |
| 15 | 12.49 | 9.07 | 5.86 | 5.30 | 7.88 |
| 20 | 15.28 | 12.09 | 8.83 | 6.48 | 8.81 |
| 25 | 15.87 | 18.69 | 10.05 | 8.16 | 9.99 |
| 30 | 18.29 | 27.05 | 12.82 | 10.41 | 11.74 |
| 35 | 23.70 | 37.96 | 16.98 | 14.98 | 14.58 |
| 40 | 30.95 | 55.05 | 23.61 | 18.76 | 19.34 |
| 45 | 43.51 | 69.84 | 33.11 | 28.30 | 28.32 |
| 50 | 59.71 | 86.26 | 46.74 | 40.73 | 43.86 |
| 55 | 83.69 | 98.40 | 66.22 | 59.86 | 58.57 |
| 60 | 113.19 | 111.09 | 90.44 | 79.20 | 82.18 |
| 65 | | | 109.08 | 96.37 | 109.50 |
| 70 | | | | 108.10 | |

The MOTE/DMTE blends (Examples 8-10) were found to be more effective and efficient heat stabilizers in terms of initial (0-20 min test), mid-term (20-50 min test) and long-term (>50 min. test) static heat stability than the individual components (Control Examples 6-7) added at 1.2 parts into the PVC film compounds. Example 9 (60/40 DMTE/MOTE) was the most effective (Table 5). This result is unexpected, since the calculated tin content of these blends is lower than that of pure DMTE (Table 3).

The dynamic heat stability results (in Yellowness index) for Control Examples 1-2 and Examples 3-5 are shown in Table 6.

TABLE 6

| Time, min. | Control Example 1 | Control Example 2 | Example 3 | Example 4 | Example 5 |
|---|---|---|---|---|---|
| 3 | 7.61 | 3.19 | 4.20 | 4.27 | 5.16 |
| 6 | 11.76 | 4.88 | 5.10 | 5.35 | 6.19 |
| 9 | 13.71 | 6.93 | 6.32 | 6.38 | 7.45 |
| 12 | 15.14 | 11.31 | 8.15 | 7.88 | 8.46 |
| 15 | 17.94 | 24.13 | 10.42 | 9.83 | 10.34 |
| 18 | 21.53 | 40.70 | 15.40 | 13.09 | 13.03 |
| 21 | 21.20 | 73.92 | 24.22 | 19.70 | 16.30 |
| 24 | 26.22 | 83.38 | 48.66 | 34.05 | 23.18 |
| 27 | 44.43 | 93.39 | 75.83 | 57.91 | 36.50 |
| 30 | 75.11 | 109.62 | 93.40 | 97.51 | 66.15 |
| 33 | 122.19 | | 114.38 | | 106.04 |
| 36 | 131.71 | | | | 119.85 |

The MOTE/DMTE blends (Examples 3-5) were found to be more effective and efficient heat stabilizers in terms of mid-term (10-30 min test) and long-term (>30 min. test) dynamic heat stability than the individual components (Control Examples 1-2) added at 1.5 parts into the PVC film compounds. The 80/20 DMTE/MOTE blend of Example 5 was the most effective (Table 6). This result is unexpected, since the calculated tin content of these blends is lower than that of pure DMTE (Table 3).

The dynamic heat stability results (in Yellowness Index) for Control Examples 6-7, and Examples 8-10 are shown in Table 7.

TABLE 7

| Time, min. | Control Example 6 | Control Example 7 | Example 8 | Example 9 | Example 10 |
|---|---|---|---|---|---|
| 3 | 9.70 | 4.51 | 6.24 | 4.56 | 6.06 |
| 6 | 14.79 | 5.63 | 6.62 | 5.43 | 7.31 |
| 9 | 17.57 | 8.13 | 8.04 | 7.06 | 8.92 |
| 12 | 19.33 | 16.39 | 10.72 | 9.60 | 11.31 |
| 15 | 22.55 | 38.73 | 16.98 | 13.80 | 15.32 |
| 18 | 29.53 | 67.23 | 29.76 | 22.60 | 21.64 |
| 21 | 42.93 | 81.39 | 57.51 | 41.74 | 35.90 |
| 24 | 86.46 | 104.98 | 83.98 | 75.21 | 74.05 |
| 27 | 127.37 | | 106.46 | 100.80 | 112.42 |
| 30 | 139.28 | | 123.16 | 119.68 | 124.74 |

The MOTE/DMTE blends (Examples 8-10) were found to be more effective and efficient heat stabilizers in terms of mid-term (10-30 min test) and long-term (>30 min. test) dynamic heat stability than the individual components (Control Examples 6-7) added at 1.2 parts into the PVC film compounds. The 60/40 DMTE/MOTE blend of Example 9 was the most effective (Table 7). This result is unexpected, since the calculated tin content of these blends is lower than that of pure MITE (Table 3).

PVC Sheet Compound Testing

Control Examples 11 and 12, and Examples 13-15 for the PVC sheet compound testing were prepared by blending various heat stabilizer compositions at 1.8 phr with the PVC sheet compound for testing. The PVC sheet compound contained 100 parts Solvin 257 RF (PVC resin), 1.5/0.8 parts Paraloid K125/K175 (modifiers), 0.4 parts Loxiol (G13, 0.4 parts Loxiol G 40, 0.3 parts Loxiol G 53, 0.1 parts AC 392 (lubricant from Honeywell International Inc.), 4 parts Kronos 2220 (TiO$_2$), and 5 parts Omya 95T (calcium carbonate). The stabilizer blends used for Control Examples 11 and 12, and Examples 13-15 are shown in Table 8.

TABLE 8

| Stabilizer components, wt % | Control Example 11 | Control Example 12 | Example 13 | Example 14 | Example 15 |
|---|---|---|---|---|---|
| DMTE | 100 | | 50 | 60 | 80 |
| MOTE | | 100 | 50 | 40 | 20 |

Control Examples 16 and 17, and Examples 18-20 were prepared by blending various heat stabilizer compositions with a clear, rigid PVC compound for film testing as with Control Examples 11-12 and Examples 13-15, except that they were added in an amount of 2.5 phr. The stabilizer blends for Control Example 16 and 17, and Examples 18-20 are shown in Table 9.

TABLE 9

| Stabilizer components, wt % | Control Example 16 | Control Example 17 | Example 18 | Example 19 | Example 20 |
|---|---|---|---|---|---|
| DMTE | 100 | | 50 | 60 | 80 |
| MOTE | | 100 | 50 | 40 | 20 |

Static and dynamic heat stability testing was performed on Control Examples 11-12 and 16-17, and Examples 13-15 and 18-20. Results are shown in Tables 10-13.
The static heat stability results for Control Examples 11-12, and Examples 13-15 are summarized in Table 10.

TABLE 10

| Time, min. | Control Example 11 | Control Example 12 | Example 13 | Example 14 | Example 15 |
|---|---|---|---|---|---|
| 0 | 27.44 | 22.74 | 22.89 | 24.05 | 23.87 |
| 5 | 28.26 | 25.75 | 24.76 | 26.13 | 25.21 |
| 10 | 29.77 | 29.19 | 27.26 | 27.94 | 27.04 |
| 15 | 36.13 | 36.23 | 31.92 | 32.80 | 32.80 |
| 20 | 43.47 | 43.87 | 39.54 | 40.03 | 38.88 |
| 25 | 50.89 | 52.00 | 49.11 | 49.37 | 48.80 |
| 30 | 66.34 | 62.39 | 59.19 | 60.31 | 59.45 |
| 35 | 86.54 | 75.70 | 72.01 | 73.52 | 73.05 |
| 40 | 105.44 | 90.81 | 87.55 | 89.07 | 89.99 |
| 45 | | 108.03 | 102.26 | 104.79 | 105.74 |

The MOTE/DMTE blends (Examples 13-15) were found to be more effective and efficient heat stabilizers in terms of initial (0-10 min test), mid-term (10-30 min test) and long-term (>30 min, test) static heat stability than the individual components (Control Examples 11-12) added at 1.8 parts into the PVC compact sheet compounds. All three tested DMTE/MOTE blends were of about the same comparable effectiveness (Table 10), This result is unexpected, since the calculated tin content of these blends is lower than that of pure DMTE (Table 3).
The static heat stability results for Control Examples 16-17 and Examples 18-20 are summarized in Table 11.

TABLE 11

| Time, min. | Control Example 16 | Control Example 17 | Example 18 | Example 19 | Example 20 |
|---|---|---|---|---|---|
| 0 | 23.49 | 20.96 | 20.69 | 21.02 | 22.92 |
| 5 | 24.60 | 22.69 | 23.76 | 21.93 | 23.48 |
| 10 | 25.86 | 24.58 | 25.20 | 23.98 | 23.62 |
| 15 | 32.04 | 29.74 | 28.64 | 26.87 | 27.38 |
| 20 | 39.44 | 38.26 | 34.01 | 32.15 | 33.39 |
| 25 | 44.89 | 44.93 | 41.19 | 41.36 | 39.53 |
| 30 | 53.01 | 53.17 | 49.27 | 49.58 | 46.38 |
| 35 | 65.86 | 62.42 | 58.06 | 60.20 | 57.49 |
| 40 | 82.89 | 70.53 | 71.62 | 71.26 | 68.02 |
| 45 | 97.26 | 85.07 | 83.95 | 86.38 | 81.16 |
| 50 | 113.13 | 98.78 | 97.15 | 99.07 | 93.39 |

The 50/50 MOTE/DMTE blend of Example 18 was found to be a more effective and efficient heat stabilizer in terms of initial (0-10 min test), mid-term (10-30 min test) and long-term (>30 min. test) static heat stability than the individual components (Control Examples 16-17) added at 2.5 parts into the PVC compact sheet compounds (Table 11). This result is unexpected, since the calculated tin content of these blends is lower than that of pure DMTE (Table 3).

The dynamic heat stability results for Control Examples 11-12 and Examples 13-15 are summarized in Table 12.

TABLE 12

| Time, min. | Control Example 11 | Control Example 12 | Example 13 | Example 14 | Example 15 |
|---|---|---|---|---|---|
| 3 | 30.89 | 31.84 | 30.27 | 30.02 | 29.01 |
| 6 | 40.31 | 37.89 | 38.72 | 36.90 | 34.73 |
| 9 | 47.51 | 45.65 | 44.37 | 43.64 | 42.58 |
| 12 | 52.79 | 52.23 | 50.24 | 49.31 | 48.89 |
| 15 | 56.81 | 57.02 | 54.88 | 56.01 | 55.59 |
| 18 | 62.10 | 64.04 | 60.68 | 62.54 | 61.42 |
| 21 | 68.90 | 72.55 | 66.58 | 69.57 | 68.92 |
| 24 | 75.86 | 80.02 | 72.29 | 76.42 | 77.49 |
| 27 | 82.80 | 86.44 | 78.53 | 83.17 | 81.44 |
| 30 | 93.21 | 95.91 | 86.33 | 88.69 | 85.48 |
| 33 | 97.60 | 97.62 | 94.50 | 95.23 | 93.25 |
| 36 | 104.54 | 89.91 | 98.27 | 99.49 | 100.29 |

The MOTE/DMTE blends (Examples 13-15) were found to be more effective and efficient heat stabilizers in terms of mid-tem (10-30 min test) and long-term (>30 min. test) dynamic heat stability than the individual components (Control Examples 11-12) added at 1.8 parts into the PVC compact sheet compounds. All three tested DMTE/MOTE blends of Examples 13-15 were comparable in terms of their stabilizing efficiencies (Table 12). This result is unexpected, since the calculated tin content of these blends is lower than that of pure DMTE (Table 3).

The dynamic heat stability testing results (in Yellowness Index) for Control Examples 16-17 and Examples 18-20 are summarized in Table 13.

TABLE 13

| Time, min. | Control Example 16 | Control Example 17 | Example 18 | Example 19 | Example 20 |
|---|---|---|---|---|---|
| 3 | 35.75 | 33.90 | 33.09 | 31.85 | 32.61 |
| 6 | 45.48 | 45.47 | 43.21 | 41.41 | 43.15 |
| 9 | 53.13 | 56.02 | 52.63 | 50.09 | 51.87 |
| 12 | 59.98 | 65.89 | 61.58 | 59.08 | 59.98 |
| 15 | 67.60 | 76.66 | 70.82 | 67.43 | 69.23 |
| 18 | 77.27 | 89.71 | 79.64 | 76.27 | 76.89 |
| 21 | 84.75 | 98.22 | 89.24 | 84.36 | 82.23 |
| 24 | 91.95 | 86.42 | 97.58 | 90.67 | 90.95 |
| 27 | 96.35 | | 88.03 | 98.06 | 97.09 |
| 30 | 106.68 | | | | 97.42 |

The MOTE/DMTE blends (Examples 18-20) were found to be more effective and efficient heat stabilizers in terms of initial (0-10 min test), mid-term (10-20 min test) and long-term (>20 min. test) dynamic heat stability than the individual components (Control Examples 16-17) added at 2.5 parts into the PVC compact sheet compounds. The 50/50 DMTE/MOTE blend of Example 18 was the most efficient compared with both Example 19 and Example 20 (Table 13). This result is unexpected, since the calculated tin content of these blends is lower than that of pure DMTE (Table 3).

We claim:

1. A heat stabilizer composition comprising:
   a) at least one mono-octyltin compound (n-Oc)Sn(T)$_3$ having a purity greater than 85 wt %; and
   b) at least one di-methyltin compound (Me)$_2$Sn(T)$_2$ having a purity greater than 85 wt %, wherein T is selected from mercaptoacetate esters, 2-ethylhexylmercaptoacetate esters, iso-octylmercaptoacetates, iso-butylmercaptoacetates, mercaptoacetate, carboxylates, maleates, diketonates, or alcoholates, and the (n-Oc)Sn(T)$_3$/(Me)$_2$ Sn(T)$_2$ ratio ranges from 10/90 to 90/10.

2. The heat stabilizer composition of claim 1, wherein T is 2-ethylhexyl mercaptoacetate.

3. The heat stabilizer composition of claim 1, wherein the (n-Oc)Sn(T)$_3$/(Me)$_2$Sn(T)$_2$ ratio ranges from 10/90 to 60/40.

4. A stabilized chlorine-containing polymer compound comprising a chlorine-containing polymer and a heat stabilizer composition, the heat stabilizer composition comprising:
   a) at least one mono-octyltin compound (n-Oc)Sn(T)$_3$ having a purity greater than 85 wt %; and
   b) at least one di-methyltin compound (Me)$_2$Sn(T)$_2$ having a purity greater than 85 wt %, wherein T is selected from mercaptoacetate esters, 2-ethylhexylmercaptoacetate esters, iso-octylmercaptoacetates, iso-butylmercaptoacetates, mercaptoacetate, carboxylates, maleates, diketonates, or alcoholates, and the (n-Oc)Sn(T)$_3$/(Me)$_2$ Sn(T)$_2$ ratio ranges from 10/90 to 90/10.

5. The stabilized chlorine-containing polymer compound of claim 4 wherein the chlorine-containing polymer is PVC.

6. A process comprising blending a chlorine-containing polymer and a heat stabilizer composition comprising:
   a) at least one mono-octyltin compound (n-Oc)Sn(T)$_3$ having a purity greater than 85 wt %; and
   b) at least one di-methyltin compound (Me)$_2$Sn(T)$_2$ having a purity greater than 85 wt %, wherein T is selected from mercaptoacetate esters, 2-ethylhexylmercaptoacetate esters, iso-octylmercaptoacetates, iso-butylmercaptoacetates, mercaptoacetate, carboxylates, maleates, diketonates, or alcoholates, and the (n-Oc)Sn(T)$_3$/(Me)$_2$ Sn(T)$_2$ ratio ranges from 10/90 to 90/10.

7. The heat stabilizer composition of claim 1 wherein (n-Oc)Sn(T)$_3$ is mono-octyltin tris(2-ethylhexyl mercaptoacetate) and (Me)$_2$Sn(T)$_2$ is dimethyltin bis(2-ethylhexyl mercaptoacetate).

8. The heat stabilizer composition of claim 1 wherein the purity of the mono-octyltin compound (n-Oc)Sn(T)$_3$ is greater than 90 wt %.

9. The heat stabilizer composition of claim 1 wherein the purity of the mono-octyltin compound (n-Oc)Sn(T)$_3$ is greater than 90 wt % to 99 wt %.

10. The heat stabilizer composition of claim 8 wherein the purity of the mono-octyltin compound (n-Oc)Sn(T)$_3$ is in the range of 92 to 99 wt %.

11. The heat stabilizer composition of claim 1 wherein the purity of the di-methyltin compound (Me)$_2$Sn(T)$_2$ is greater than 90 wt %.

12. The heat stabilizer composition of claim 1 wherein the purity of the di-methyltin compound (Me)$_2$Sn(T)$_2$ is greater than 90 wt % to 99 wt %.

13. The heat stabilizer composition of claim 11 wherein the purity of the di-methyltin compound (Me)$_2$Sn(T)$_2$ is in the range of 92 to 99 wt %.

14. The heat stabilizer composition of claim 7 wherein the ratio of mono-octyltin tris(2-ethylhexyl mercaptoacetate)/dimethyltin bis(2-ethylhexyl mercaptoacetate) ratio ranges from 20/80 to 50/50.

* * * * *